United States Patent
Kozee et al.

(10) Patent No.: US 9,034,090 B2
(45) Date of Patent: May 19, 2015

(54) WETNESS INDICATING INK COMPOSITIONS

(75) Inventors: Michael Kozee, Wheaton, IL (US); Linfang Zhu, Woodridge, IL (US)

(73) Assignee: Videojet Technologies Inc., Wood Dale, IL (US)

( * ) Notice: Subject to any disclaimer, the term of this patent is extended or adjusted under 35 U.S.C. 154(b) by 66 days.

(21) Appl. No.: 13/576,450

(22) PCT Filed: Feb. 18, 2011

(86) PCT No.: PCT/US2011/025363
§ 371 (c)(1),
(2), (4) Date: Aug. 1, 2012

(87) PCT Pub. No.: WO2011/103378
PCT Pub. Date: Aug. 25, 2011

(65) Prior Publication Data
US 2012/0308787 A1 Dec. 6, 2012

Related U.S. Application Data

(60) Provisional application No. 61/305,822, filed on Feb. 18, 2010.

(51) Int. Cl.
| | | |
|---|---|---|
| *C09D 11/02* | (2014.01) | |
| *B41J 3/407* | (2006.01) | |
| *C09D 11/328* | (2014.01) | |
| *C09D 11/38* | (2014.01) | |
| *B41M 5/00* | (2006.01) | |
| *A61F 13/42* | (2006.01) | |

(52) U.S. Cl.
CPC ........... *B41J 3/407* (2013.01); *C09D 11/328* (2013.01); *C09D 11/38* (2013.01); *B41M 5/0023* (2013.01); *A61F 13/42* (2013.01)

(58) Field of Classification Search
USPC ....................... 106/31.37; 347/100
See application file for complete search history.

(56) References Cited

U.S. PATENT DOCUMENTS

| | | |
|---|---|---|
| 4,877,719 A | 10/1989 | Higashi et al. |
| 4,909,879 A | 3/1990 | Ball |
| 5,255,020 A | 10/1993 | Martin et al. |
| 5,531,818 A | 7/1996 | Lin et al. |
| 5,973,025 A | 10/1999 | Nigam et al. |
| 6,083,310 A | 7/2000 | Peterson et al. |
| 6,383,274 B1 | 5/2002 | Lin |
| 7,285,160 B2 | 10/2007 | Zhu et al. |
| 7,332,642 B2 | 2/2008 | Liu |
| 2005/0092204 A1* | 5/2005 | Zhu et al. ............ 106/31.58 |
| 2006/0149198 A1 | 7/2006 | Liu |
| 2006/0236470 A1* | 10/2006 | Sabnis et al. ............ 8/405 |
| 2012/0157948 A1* | 6/2012 | Nhan et al. ............ 604/361 |
| 2013/0178810 A1* | 7/2013 | Liu ................ 604/361 |

* cited by examiner

*Primary Examiner* — Veronica F Faison
(74) *Attorney, Agent, or Firm* — Joseph A. Yosick

(57) ABSTRACT

A method of printing on a hygienic article includes applying droplets of an ink composition with an ink jet printer to a surface of a hygienic article to form a desired image. The ink composition includes an organic solvent, a water-soluble binder resin including hydroxypropylcellulose, and a water-soluble dye. The image acts as a wetness indicator by dissolving in an aqueous fluid.

22 Claims, No Drawings

WETNESS INDICATING INK COMPOSITIONS

RELATED APPLICATIONS

This application claims priority under 35 U.S.C. §371 from PCT Application No. PCT/US2011/025363, filed in English on Feb. 18, 2011, which claims the benefit of U.S. Provisional Application No. 61/305,822, filed Feb. 18, 2010, the disclosures of both of which are incorporated herein by reference in their entireties.

BACKGROUND OF THE INVENTION

The present disclosure relates to methods of printing wetness indicators on hygienic articles.

Methods have been proposed to indicate wetness in a hygienic article, namely diapers or incontinence pads. For example, the inner surface (or the surface towards the body) of the outer liner of a diaper may have a printed message such as animal figures, alphabets, or other patterns attractive to children (infants or toddlers). When the diaper becomes wet and the urine reaches the outer liner, the figure or pattern in the printed message will dissolve or otherwise be changed. Such changes in the image will be visible to the wearer or caregiver, thereby indicating that a diaper change is required.

Ink jet printing is a well-known technique by which printing is accomplished without contact between the printing device and the substrate on which the printed characters are deposited. Briefly described, ink jet printing involves projecting a stream of ink droplets to a surface in a controlled manner so that the droplets are caused to form the desired printed image on that surface. This technique of noncontact printing is particularly well suited for the application of characters onto substrates such as diapers. Ink jet printing can be broadly divided into drop-on-demand (DOD) printing, and continuous inkjet (CIJ) printing. In DOD printing, droplets are produced as needed by the movement of the piezo or the generation of a bubble to form an image on the substrate. The latter is known as thermal ink jet (TIJ). In CIJ printing, drops are produced continuously, but only a fraction of the drops are used to form an image. During CIJ printing, the drops are selectively charged and deflected in an electrical field. Printed drops are charged and deflected to form the print image and the non-charged drops are returned to the gutter. The amount of charge determines the relative position of the printed drops on the substrate. In binary array technology, the non-printed drops are charged and deflected to the gutter and the printed drops are not charged. As is the case with DOD technology, the relative positions of the nozzles in the array determine the relative position of the printed drops.

There are several advantages with the binary array technology. In comparison to the single nozzle CIJ technology, binary array printing technology offers better print quality because the alignment of the printed drops does not depend on the ability to accurately charge these drops. In addition, due to the number of nozzle orifices in the array, binary array is particularly advantaged to print large graphics or multiple line images at high line speed.

For the production of hygienic articles, inks are preferably laid down within a single pass of the printhead over the same area of the substrate and printers should be easily incorporated into existing production lines. Digital printers based on DOD Piezo or TIJ technology can not typically apply enough ink volume during a single pass at very high speeds to achieve a high degree of print color contrast. A virtue of binary array printing technology over drop-on-demand ink jet is the delivery of relatively large volume ink jet drop. Multiple drops can also be applied at essentially the same physical spot to promote the printed color and contrast. In addition, piezo DOD inks are typically based on oil or other non-volatile solvents and thus do not dry on non-porous or semi-porous substrates. TIJ inks are typically water based but typically contain a substantial amount of non-volatile solvents, again not suited for printing on non-porous and semi-porous plastic films or non-woven materials. In addition, drop generation rates of CIJ printing are higher than those of either DOD or TIJ printing. As a consequence of all of these factors, the line speed of DOD or TIJ printing is much slower than the CIJ binary array. Conventional contact printing methods such as flexography require a relatively large footprint on a production line and thus are not preferred for reasons of inconvenience and cost of integration.

One type of TIJ-based technology that resembles binary array is Kodak STREAM, which has recently been introduced. Kodak STREAM is a continuously recirculating ink technology, but instead of using a piezo signal to induce drop breakoff, it uses a modulated series of thermal pulses at each of the individual nozzles. Like binary array, STREAM's is theoretically capable of forming printing drops at a rate exceeding 100 thousand per second, so it would be also be suited to very high speed, high quality printing of hygienic articles if suitable fast-drying inks were to be employed.

In general, an ink jet ink composition must meet certain strict requirements to be useful in ink jet printing operations. These requirements relate to the physical properties of the fluid (such as viscosity and resistivity), the chemical properties (such as the solubility and compatibility of the components), and the ability to suitably wet the substrate. Further, the ink must be quick drying and smear resistant, and be capable of passing through the ink jet nozzle(s) without clogging, and permit rapid cleanup of the machine components with minimum effort.

Previous wetness indication ink jet inks have dry times on non-porous substrates greater than 3 seconds, and most are greater than 5 seconds. In addition, such inks are typically not designed for binary array printers.

BRIEF SUMMARY OF THE INVENTION

The disclosure provides methods of printing an image to serve as a wetness indicator on hygienic articles.

In one aspect, a method of printing on a hygienic article includes applying droplets of an ink composition with an ink jet printer to a surface of a hygienic article to form a desired image. The ink composition includes an organic solvent, a water-soluble binder resin including hydroxypropylcellulose with a molecular weight of between 10 kDaltons and 90 kDaltons, and a water-soluble dye. The image acts as a wetness indicator by dissolving in an aqueous fluid.

In another aspect, an ink jet ink composition includes a ketone solvent, a water-soluble binder resin, and a water-soluble dye. The ink composition has a dry time of one second or less when printed on a semi-porous surface using a binary array printer.

In another aspect, a hygienic article includes a body contacting surface and a garment contacting surface opposite the body contacting surface. An image printed by ink jet printing is visible through either the body contacting surface or the garment contacting surface. The image is formed from an ink composition comprising a water-soluble dye and a water-soluble resin derived from a carbohydrate. The image provides an aqueous wetness indicator.

DETAILED DESCRIPTION OF THE INVENTION

The disclosure relates to methods of printing wetness indicators on hygienic articles, such as baby diapers, adult incontinence pads, or feminine pads. The printing method uses digital ink jet printing systems, particularly binary array ink jet printers. The disclosure provides a single-pass printing system capable of printing digital images at speeds that are compatible with the production line speeds that are typically employed in the hygienic article industry, with the requisite ink drying rates required to prevent buildup of ink on production line components or smearing of the printed image. The wetness indicator image changes or dissolves when exposed to water or bodily fluids to provide an indication that the diaper or other hygienic article has been soiled. This indicator thus provides a visual cue to the wearer or the caregiver that the article needs to be changed.

The method of printing on a hygienic article includes applying droplets of an ink composition with an ink jet printer to a surface of a hygienic article to form a desired image. Ink jet printing is defined broadly as any category of inkjet including DOD piezo, DOD thermal inkjet, STREAM, continuous inkjet, binary array continuous or the like. The ink jet printer is preferably a binary array continuous inkjet printer.

The printed images should have sufficient visibility or contrast and a desired color when printed on non-porous or semi-porous plastic films and non-woven fabric materials. The image may be any suitable color as defined by the Pantone color space or other equivalent methods. The wetness indicator image should dissolve rapidly when exposed to water or bodily fluids to provide a timely indication that the diaper or other hygienic article is soiled. But, concurrently, the image should not dissolve prematurely or be easily degraded after exposure to high ambient humidity levels.

The dry time of the ink composition is preferably short at the instant of printing onto the hygienic article. For example, the dry time is preferably 5 seconds or less, preferably 2 seconds or less, more preferably 1 second or less, and most preferably 0.5 seconds or less, when printed on the film comprising the outer article liner, in a single printing pass at print densities of at least 100×100 dots per inch (such as 128×128 dpi), at an ambient temperature between 20 and 35° C., and at a relative humidity of 10-70%. The ink compositions preferably have a dry time of one second or less without the need for secondary processes such as physical drying methods. Dry times 0.5 or 0.2 seconds or less are particularly preferred. Competitive digital printing methods that do not use secondary drying methods are generally limited to slow drying inks (>3 seconds).

Dry times are assessed in the following manner. If performing comparative dry time tests between different ink compositions, a printed image can be rubbed lightly with a finger immediately after printing. The minimum time that no smudging occurs in the printed image is the dry time. Time can be kept by a conventional stopwatch; however, only dry times of greater than or equal to about two seconds can be accurately determined this way. A second method is preferred for measuring dry less than two seconds. In this method, the printed image is passed via a conveyor underneath a fixed pickup roller at an approximately constant downward pressure of five kilograms against the substrate. The image is printed at with a maximum density defined by a maximum horizontal and vertical dot pitch (128×128 dpi in the case of the Videojet BX™ array printer). The contact time to the roller is calculated by dividing the distance by the linespeed (i.e., 1.0 feet divided by 5 feet/second=0.2 seconds or 200 milliseconds) and is varied by moving the position of the roller relative to the printing nozzles and adjusting the linespeed. The dry time for a given printed image is then defined to be the lowest test time where no pickup or transfer is visually observed on the pickup roller. A suitable transfer roller material would be PVC marking tape, as that which is available from 3M Inc. For comparative testing between different ink compositions, the tests should be conducted at controlled ambient conditions: i.e., less than about 40% R.H. at 23±3° C.

Even though the dry times specified herein meet the requirements of the intended applications, any processes to increase drying rate can be employed prior to or subsequent to printing. These processes include using chemical pretreatments or posttreatments. Other processes include either pre-heating or post-heating the substrate or heating at the point of printing such that the ambient temperature is higher. Heating may be provided by any means including IR such as provided by ceramic heating elements, visible or full-spectrum light sources (i.e., blackbody sources), radiant heat, forced heated air, laser, LED lighting, etc. Either heated or unheated air streams may be directed onto the freshly printed image. This may be provided by an air knife or similar compressed air source employing a stream-directing nozzle. The compressed air may be provided by external sources or may be provide as output by the printer itself. The compressed air is preferably dried air with volumetric water content below 25 g/m$^3$.

Most ink jet ink compositions are not specifically formulated with respect to good operation in either continuous inkjet printers or binary array printers. In order to work in binary array and continuous ink jet printers, the ink compositions need to possess fundamental physical properties—e.g., viscosity, velocity of sound, surface tension—that lends toward Rayleigh instability within the bounds set by the drop generator including the drop generation frequency, modulation amplitude and ink cavity dimensions, etc. The ink compositions described herein can, by changing the modulation amplitude alone, achieve a state of Rayleigh breakoff, particularly one wherein the drop tail, along with all the satellites formed thereof, merge with the printing drops within the drop flight time to the substrate. A satellite is defined as a small drop separated from the main drop during the drop break-off process. Unlike DOD devices where drops are generated from a standing reservoir, binary array ink streams are under continuous pressure and use a single piezo induced pulse to generate droplets across a large array of nozzles. The ability to eliminate drop satellites by tailoring the modulation pulses as described above provides better print quality than conventional DOD inkjet printers especially at high linespeeds, since in the latter, the tails and/or satellites would be visibly divergent from the main drop in the printed image. In addition to adversely affecting print quality, satellite drops also have deleterious effects because they are not charged and deflected correctly by the electrostatic deflection mechanism employed in the Videojet BX and thus would be more prone to build up on components inside the head rather than being recycled within the ink management system leading to printing failures. The ink compositions of the current disclosure contain resins that due to their chemical structures increase the effective modulation voltage amplitude range where satellite-free operation is possible. Furthermore, the ink components including the resins disclosed herein achieve a state where the drop tail length is minimized at the point of drop breakoff from the ink stream. This has the positive impact on the print window as described above and furthermore results in relatively low mist generation at the point of breakoff. Any mist generated will naturally impact the surfaces near the ink stream and excessive mist generation will negatively impact run time and reliability. Such formulation resins are initially selected based on the criteria of exhibiting a discrete favorable molecular weight range. The exact weight range, however, is dependent on the molecular structure of the resin and can only empirically be determined for any given resin chemical class. Thus, the molecular weight of the resin is crucial to obtaining acceptable print performance in binary array and continuous ink jet printers.

The printing system is preferably a binary array printing system, preferably a BX printer available from Videojet Technologies Inc, the Videojet® BX6000 series (single head and dual headed versions). The BX printing system delivers a number of advantages regarding reliability in industrial applications by virtue of its design. For printing on hygienic articles, it is desirable to be able to print an image at least 2 inches wide with 128 dpi resolution (horizontal and vertical). High speed digital printing methods are generally limited to a width of a few inches. The printer is preferably capable of printing with the desired print quality while the substrate is moving at a high speed. For example, the hygienic article may move with respect to the ink jet printer at a speed of greater than 1000 ft/min, or greater than 1500 ft/min, or greater than 1750 feet/min, or greater than 2000 ft/min during printing.

The ink composition includes a solvent, a water-soluble binder resin, and a water-soluble dye. The solvent is preferably a ketone or alcohol solvent. The binder resin is preferably derived from a carbohydrate. The ink composition may also include a water soluble or water insoluble conductive agent.

The ink compositions disclosed herein are both fully aqueous washable and especially suited to the binary array printing process. Water soluble resins and dyes typically are not sufficiently soluble in fast drying organic solvents such as ketones. The resin preferably has very high bulk water solubility. In embodiments, the water-soluble resin has a bulk solubility of 100 g/L or more, preferably 200 g/L or more, and more preferably 500 g/L or more, in water at a temperature of 20 to 40° C. and pH of between 4 and 9. The water-soluble resin is stable in solvents and, for example, can be cast as a dry film from acetone and completely resolubilized in acetone many times without any reduction in the film's solvent or water resolubility. The resins and dyes are further selected so that the ink compositions physical properties—e.g., viscosity and filterability—are stable over a period of accelerated aging simulating the ink's shelf life. The high water solubilities of the resin and dye facilitate removal of the printed message when contacted with urine or other aqueous fluids. The printed image should be completely washable in aqueous fluids exhibiting a pH range between 4 and 9. The water-soluble resin further acts as a binder with the requisite adhesion to the plastic substrate. The image should remain as originally printed on the hygienic article for 24 months or longer without need for secondary treatments after packaging. Within 1 minute after printing, the image should withstand abrasive rubbing (i.e., a dry thumb rub) without removal and remain so throughout its life prior to activation by an aqueous fluid.

As previously described, the printing method may be used for any type of hygienic article. The hygienic article (such as a diaper) may include a plurality of component materials. For example, a diaper may include a backsheet, a topsheet, an acquisition layer, and an absorbent core disposed between a body contacting surface and a garment contacting surface. The outermost surface of the backsheet may form the garment contacting surface, while the innermost surface of the topsheet may form the body contacting surface. The backsheet typically serves to both encase the absorbent components and provide the printing substrate for the user visible graphics. It is also termed the 'outer liner' for sake of clarity herein.

As previously described, the hygienic articles include an image that acts as a wetness indicator. The image preferably changes from a colored image to colorless or otherwise diffused to indicate the article is wet. The wetness indicator image can be located on or against any surface of a component material, including the body contacting surface and the garment contacting surface, provided that the wetness indicator remains visible from the exterior of the absorbent article. Examples of the location include the backsheet, the topsheet, the acquisition layer, and the absorbent core. The preferred printing surface is the inside surface of the backsheet (also described as the outer liner).

The substrate comprising the outer liner is generally a plastic film but may be more specifically a nonporous or semi-porous plastic film or a nonwoven plastic surface. The substrate may further include a composite between a film and a second material consisting of a woven or non-woven fabric made from either naturally occurring or synthetic fibers or combinations thereof. Substrates of particular interest are semi-porous plastic films that are commonly used to enhance the resilience of the overall diaper construct. As visible under high magnification, the surfaces of such material tend to be porous with features on the order of less than 100 microns comprising microfibrous networks, pits, valleys and/or actual through-holes/pores. The substrates may be translucent without pigmentation or opaque or semi-opaque comprising inorganic filler as pigmentation within the substrate matrix. The construction materials are most typically polyethylene or polypropylene, but may be made of any suitable plastic material. The images should have good print quality on such substrates which generally will exhibit surface energies between 20 and 50 dynes/cm.

The water soluble nature of the composition printed at the specified printing location within the article and upon the specified kind of substrate material each lend to the property that the printed images are removed or changed upon contact with aqueous fluids such as urine. This removal may be complete in that the dye is physically separated from the printed article by fluid dynamic forces such as Brownian motion, capillary action, etc. The removal may be partial, such that only a portion of the image is intended to be removed. The images may rather be changed and not removed so that they blur or distort as a result in the migration of the dye to the immediate surfaces surrounding the image. This change may occur at any desired rate, but wetness indicators such that are employed in current incontinence products function rapidly and so it is preferred that, upon contact with excess aqueous fluids, the image change or removal should occur within one minute or preferably 10 seconds or less, or more preferably less than 1 second. The removal rate and/or degree can be determined by any suitable method. For example, the printed substrate can be immersed in a test fluid, e.g., deionized or tap water, for a predetermined period of time and subsequently removed and allowed to dry. The residual color on the substrate can then be measured.

Methods to determine the relative removability degree include PCR (Print Contrast Ratio), Optical Density (OD) or PCS (Print Contrast Signal) measurements. Preferred methods are to use a spectrodensitometer (such as an Xrite Series 500 Spectrodensitomer) to provide either optical density or $\Delta E$ values; i.e., $L^*a^*b^*$ values. As is understood in the art, these values can be used to calculate the $\Delta E$ differences between the printed samples and the unprinted substrate as a background. A ΔE from background of less than 4 is defined as barely visible and indicates a sufficient degree of removal during soaking. A ΔE color change between pre-exposed and post-exposed printed samples of at least 20 is defined as a suitably perceptible color change to provide the users positive wetness indication. The inventive ink compositions described herein can achieve a ΔE color change between pre-exposed and post-exposed images of greater than 20 and a ΔE from background after washing of less than 4.

Turning now to the particular components that make up the ink composition, in accordance with an embodiment, the ink composition may include one or more organic solvents. The organic solvents are selected from ketones, lower order alcohols (i.e., ethanol, isopropanol, n-propanol, t-butanol, isobutanol, n-butanol), carbonates (i.e., dimethyl carbonate), glycol ethers, esters, glycol ether acetates, and mixtures thereof. The organic solvents are preferably selected from $C_1$-$C_4$ alcohols, $C_3$-$C_6$ ketones, and mixtures thereof. Examples of $C_3$-$C_6$ ketones include acetone, methyl ethyl ketone, methyl n-propyl ketone, and cyclohexanone. Examples of $C_1$-$C_4$ alcohols include methanol, ethanol, 1-propanol, n-butanol and 2-propanol. The organic solvents, particularly alcohols and ketones, have further attractive features over water based inks in that they penetrate semi- and some non-porous substrate surfaces more readily and evaporate more quickly thus reducing dry time and improving through film contrast and film adhesion.

In particular embodiments, the ink composition includes, as the organic solvent(s), acetone or a blends of acetone and lower order alcohols such as ethanol. In another embodiment, the blends may include two or more solvents comprising a ketone and a slower drying organic cosolvent. Particular preferred slower drying solvents can be selected from the following list: diacetone alcohol n-propyl acetate; n-amyl acetate; propylene glycol monomethyletheracetate; propylene glycol monopropylether; propylene glycol monomethylether; propylenglycol t-butyl ether; butyl lactate, and ethyl lacate. Inks will preferably leave no odorous traces in the packaging materials. The majority of DOD and TIJ inks for nonporous surfaces include persistent, low volatility solvents that will undesirably taint the packaging of hygienic articles. Solvents used herein can be selected such that they fully evaporate leaving no detectable or perceptible traces after printing and prior to packaging of the hygienic article. Furthermore, if lesser volatile cosolvents are employed, they can be selected from ones that exhibit little or no odor such as propylene glycol monopropylether, ethyl lactate, butyl lactate, diacetone alcohol, etc. In another preferred embodiment, the ink may largely include ethanol and isopropanol as the a component of the organic solvent. Ethanol and/or isopropanol would be a preferred in some instances over ketones based on their familiar odor and lower overall vapor pressures and potential for forming volatile organic compounds. Preferred denatured ethanol grades would not introduce any additional odorous cosolvents.

The total amount of the organic solvents can be in any suitable amount, for example, in an amount 70% or more, 80% or more, or 90% or more by weight of the ink composition. In an embodiment, the organic solvents can be present in an amount from 70% to about 99%, preferably from about 80% to about 95%, and more preferably from about 90 to about 95% of the ink composition. The ink composition can optionally include water in a suitable amount, e.g., up to 10% by weight, up to about 5% by weight, or up to about 2% by weight of the ink composition.

In an embodiment, the organic solvents used include acetone and ethanol. The acetone may be present in an amount between 40% and 99% by weight, preferably between 45% to 55% by weight, and more preferably between 48% and 52% of the ink composition. The ethanol may be present in an amount between 0.1% and 60% by weight, preferably between 30% and 50% by weight, and more preferably between 35% and 45% by weight of the ink composition.

The dye is water soluble so that it lends to the functional aqueous wetness indictor. Any water soluble colorant or combination of colorants can be employed. In some cases pigments might be suitable if they are water soluble, i.e., sulfate/sulfonate modified pigments such as carbon black. Dyestuffs are preferred and can be chosen from either naturally occurring (i.e., foodstuff extracts) or synthetic dyes. Suitable general classes of dyes are direct, acid, base, vat, reactive, mordant, and or solvent. Furthermore the selected dyes include those which structures correspond (or include the functional groups described by the following: polyene, polymethine, napthalimide, diarymethine, triarylmethine, carbonium, azaannulenes (pthalocyanines), napthol, nitro/nitroso dyes, azo dyes (mono- or disazo types), carbonyl dyes (anthraquinones, quinones, benzoquinones, indigoids, leucos), sulfur dyes, nigrosine, metal complex dyes, perylene dyes, vegetable dyes, food dyes, polymeric dyes, fluorescent/optical brighteners, etc. Examples of natural colorants include beta-carotene, annatto extract, astaxanthin, astaxanthin dimethyldisuccinate, dehydrated beets, cholorophyllin (and its copper complexes and various salts), ultramarine blue, caramel, canthaxanthine, β-Apo-8'-carotenal, β-Carotene or its derivatives, cochineal extract, grape (or skin) extract, guanine, fruit juice, vegetable juice, carrot oil, corn endosperm oil, paprika, paprika oleoresin, saffron, tomato extract (lycopene), turmeric (curcumin), amaranth, anthocyanins, azorubine, bixin, blackcurrent extract, canthaxanthin, citraxanthin, carmine, carthamus red, carthamus yellow, eosine, erythrosine, orcein/orchil, paprika extract, quercetin, persian berries, riboflavin, tagetes extract, tartrazine, ultramarines, and xanthophyll.

Particularly desirable dyes include FD&C colorants or D&C colorants (i.e., those specified by the e-CFR Title 21, part 74 regulations) in the U.S or their foreign variants (i.e., the European Union E-List and the UN FAO color list) approved for food, cosmetic or drug usage. Examples include but are not limited to FD&C Blue 1 (C.I. 42090:2), FD&C Blue No. 2, C.I. Food Blue 5, D&C Blue 4, D&C Blue 9, BLUE VRS, Brilliant Blue FCF, Patent Blue 5, FD&C Red 3, FD&C Red 4, FD&C Red 40, D&C Red 6 (C.I. 15850), D&C Red 7 (C.I. 15850:1), D&C Red 9 (C.I. 15585:1), D&C Red No. 17, D&C Red 21 (C.I. 45380:2), D&C Red 22 (C.I. 45380:3), D&C Red 27 (C.I. 45410:1), D&C Red 28 (C.I. 45410:2), D&C Red 30 (C.I. 73360), D&C Red 31, D&C Red 33 (C.I. 17200), D&C Red 34 (C.I. 15880:1), D&C Red 36, D&C Red 39, C.I. Food Red 7, Altura Red AC, Sudan Red G, Cirus Red 2, Fast Red E, Red 2G, Red 10B, Rhodamine B, Scarlet GN Ponceau 2R/4R/6R/SX, D&C Violet 2, methyl violet, Violet 5BN, Acid Fuchsin B, Benzyl Violet 4b, indigotine, FD&C Yellow 5 (C.I. 19140:1), FD&C Yellow 6 (C.I. 15985:1), FD&C Yellow 10 (C.I. 47005:1), D&C Yellow 7, D&C Yellow 8, D&C Yellow 10, D&C Yellow 11, C.I. Food Yellow 3, C.I. Food Yellow 23, chryosoine yellow, Fast Yellow AM, Napthol Yellow S, Sunset Yellow FCF, Yellow 2G, Yellow 27175N, D&C Orange 4, D&C Orange 5 (C.I. 45370: 2), D&C Orange 10, D&C Orange 11, Orange B, D&C Green 5, Orange G, Orange GN, Orange I, Orange RN, Sudan G, D&C Green 6, D&C Green 8, FD&C Green 3, Green S, Fast Green FCF, Guinea Green B, Light Green SF, D&C Brown 1, Brown FK, Brown HT, D&C Black 2, D&C Black 3, Black 7984, and Brilliant Black PN. Especially preferred dyes from this list are FD&C Blue 1, FD&C Red 3, FD&C Red 40, FD&C Yellow 5, FD&C Yellow 6, and FD&C Green 3.

Another particularly suitable class of dyes is polymeric dyes such as those sold under the tradenames Versatint, Reactint, Millijet and Polytint, available from Milliken Chemical, Inc. The chemical structures of these are specifically disclosed in U.S. Pat. No. 6,083,310, which is incorporated herein by reference. These polymeric dyes are low migratory once incorporated in a polymer matrix and are less likely to permanently stain skin and/or clothing when used on personal garments. The dyes may be further selected based on their water solubility and compatibility with the ink formulations described herein—many are both water soluble and compatible. Particularly suitable Millijet dyes are Millijet Blue 28, Millijet Red 17, Millijet Orange 31, Millijet Violet 82, and Millijet Black 40. For example, Millijet Blue 28, a triaryl methane chromophore dye, shows very good water solubility and a desired end color. In embodiments, the dye has a water solubility at 25° C. of 50 g/L or more, preferably 100 g/L or more, and more preferably 150 g/L or more. Solubility of the dye in the solvent-based ink formulations described herein is preferably greater than 20 g/L. The dye is preferably substantially soluble in water at a temperature of 20 to 40° C. and pH of between 4 and 9. The ink composition is preferably substantially free of solid particle sized eater than 1 micron.

In any of the embodiments above, the dye can be present in an amount from about 0.01% to about 10%, preferably from about 0.2% to about 7%, and more preferably from about 0.5% to about 3% by weight of the ink composition.

As discussed, the ink composition includes one or more binder resins. Any suitable binder resin, can be employed, preferably a water-soluble resin as the primary binder. In an embodiment, select non-water soluble binders can be used as coresins to impart some degree of waterfastness or humidity resistance to the main binder.

The ink preferably contains a water soluble binder that is a polymer derived from a cyclic, but non-aromatic and non-ionic, carbohydrate. It is believed that these binders generally offer the best reliability in a binary array inkjet printer. These binders include the family of sugars (sucroses, fructoses, etc.), starches, and celluloses. The resin preferably has a molecular weight (Mw) (determined by gel permeation chromotography) of less than 120 kDaltons, more preferably less than 100 kDaltons, and preferably between 10 kDaltons and 90 kDaltons, more preferably between 40 kDaltons and 80 kDaltons. The ink composition most preferably contains a cellulose-type resin as a binder. The cellulose resin may be a hydrophobic-modified cellulose such as a cellulose ester, cellulose acetate, cellulose acetate butyrate or cellulose acetate propionate, cellulose ether, ethyl cellulose, methyl cellulose, cellulose nitrate or nitrocellulose. The cellulose may alternatively be a hydrophilic cellulose such as hydroxyethyl cellulose, alkly-modified hydroxyethyl cellulose or hydroxypropyl cellulose, hydroxyethyl/hydroxypropyl cellulose copolymer, hydroxypropyl cellulose, and carboxymethyl cellulose. A preferred modified cellulose resin is hydroxypropyl cellulose which is an ether-modified cellulose formed by the reaction of raw cellulose with propylene oxide. A highly suitable resin is hydroxypropyl cellulose is HPC SSL from Nisso American Corporation, which has a molecular weight of about 60 kDaltons.

The polymeric binder resin can be present in any suitable amount, for example, in an amount from about 0.1% to about 30%, preferably from about 0.5% to about 15%, and more preferably from about 1% to about 8% of the ink composition. The ink composition preferably contains less than 6% resin solids by weight.

In a particular embodiment of the ink composition, the organic solvent or solvents can be present in an amount from about 70% to about 95% by weight, the dye can be present in amount from about 0.5% to about 3% by weight, and the binder resin can be present in an amount from about 1% to about 8% by weight of the ink composition.

The ink composition preferably has a low resistivity, such as within the range of about 20 to about 2000 ohm-cm. The desired conductivity can be achieved by the addition of an ionizable material or conductive agent. Examples of such conductive agents include ammonium, alkly-/arylammonium, alky-/arylphosphonium, alkali, and alkaline earth metal salts. Suitable anions include halides, hydroxide, borates (i.e., halo or phenyl), tosylates, triflates, thiocyanates, nitrates, sulfonates, carbonates, sulfates, acetates, etc. Specific examples of such suitable for use in the formulations described herein include ammonium hydroxide, lithium nitrate, lithium thiocyanate, lithium trifluoromethanesulfonate (triflate), sodium acetate, ammonium acetate, potassium bromide, potassium thiocyanate, dimethylamine hydrochloride, hydroxylamine hydrochloride, tetraethylammonium bromide, tetraethylammonium triflate, tetraethylammoniuim acetate, tetraethylammonium tosylate, tetrabutylphosphonium bromide, tetrapropylammonium bromide, tetraphenylphosphonium bromide, potassium tetraphenylborate, tetrabutylammonium hexafluorophosphate and tetrabutylammonium acetate. Preferred conductive agents include lithium salts such as lithium triflate or lithium nitrate and tetraethylammonium salts such as tetraethyl ammonium tosylate. Any suitable amount of the conductive agents can be used. Normally, a conductive agent content of up to about 3% by weight of the ink composition provides the desired conductivity, typically in a range of about 0.1% to about 2%. In certain cases where the dye is an ionizable species, the conductive agent may be omitted.

The ink composition can further include one or more additives such as surfactants and/or plasticizers, for example, to improve water removability or dot definition on a particular substrate. Any suitable surfactant can be used; for example, a surfactant selected from the group consisting of anionic surfactants, cationic surfactants, non-ionic surfactants, polymeric surfactants. Examples of surfactants include modified polysiloxanes, alkyl modified polyoxyalkyleneamines, alkyl modified propoxylated (poly(oxypropylene)) diamines, alkyl ether amines, nonyl phenol ethoxylates, ethoxylated fatty amines, fluorinated organic acid diethanolamine salts, alkoxylated ethylenediamines, alkyl modified polyethylene oxides, alkyl modified polyalkyleneoxides, alkyl phosphate ethoxylate mixtures, polyoxyalkylene derivatives of propylene glycol, polyoxyethylated fatty alcohols, and salt of fatty acids. A specific example of a suitable surfactant, is diethylhexyl sodium sulfosuccinate, available from Uniqema under the trade name MONOWET MO-E75).

In any of the embodiments, the surfactants can be present in an amount from about 0.001 to about 2.0%, preferably from about 0.02 to about 1%, and more preferably from about 0.03 to about 0.5% of the ink composition.

Examples of suitable plasticizers include phthalate plasticizers, e.g., alkyl benzyl phthalates, butyl benzyl phthalate, dioctyl phthalate, diisobutyl phthalate, dicyclohexyl phthalate, diethyl phthalate, dimethyl isophthalate, dibutyl phthalate, and dimethyl phthalate, esters such as di-(2-ethylhexy)-adipate, diisobutyl adipate, glycerol tribenzoate, sucrose benzoate, dibutyl sebacate, dibutyl maleate, polypropylene glycol dibenzoate, neopentyl glycol dibenzoate, dibutyl sebacate, and tri-n-hexyltrimellitate, phosphates such as tricresyl phosphate, dibutyl phosphate, triethyl citrate, tributyl citrate, acetyl tri-n-butyl citrate, polyurethanes, polyacrylics; lactates and sulfonamide plasticizers such as Plasticizer 8, available from Monsanto Co., St. Louis, Mo., which is n-ethyl o,p-toluene sulfonamide.

In certain embodiments, the plasticizer can be present in an amount from about 0.1 to about 5.0%, preferably from about 0.2 to about 3.0%, and more preferably from about 0.25 to about 2.0% of the ink composition.

The ink composition can have any suitable viscosity or surface tension. The ink composition preferably has a viscosity at 25° C. between 1 and 10 cPs, preferably between 1.5 and 8.0 cPs, and most preferably between 2.5 and 5.0 cPs. The ink composition preferably has a surface tension defined by the bubble-tensiometer method from about 20 to about 50 mN/m, from about 21 to about 40 mN/m, or from about 22 to about 30 mN/m at 25° C. The solids content of the ink composition may be less than 50% by weight, more preferably less than 20% and is most preferably less than 10% by weight. The resulting sonic velocity of the ink is preferably between 1100 and 1600 meters per second as measured by the acoustical method.

The ink composition can be prepared by any suitable method. For example, the chosen ingredients can be combined and mixed with adequate stiffing and the resulting fluid filtered to remove any undissolved impurities.

EXAMPLES

For the following Examples, several different kinds of plastic outer liner materials were evaluated as substrates for printing; each was obtained from commercial diaper products. The materials are illustrated in Table 1.

TABLE 1

| | |
|---|---|
| Diaper 1 | Smooth, microporous polyethylene sheet I |
| Diaper 2 | Fibrous non-woven bound to surface of a smooth, polyethylene sheet |
| Diaper 3 | Smooth, microporous polyethylene sheet II |
| Diaper 4 | Visually rough, microporous sheet |
| Diaper 5 | Smooth, microporous polyethylene sheet III |

The general tests of the experimental ink compositions were performed by deconstructing the store bought diapers to print on the inner (body facing) surface of the outer (clothes facing) liner. Print density was varied in some of the Examples by adjusting the pixel density in the image to be printed-100% was a fully dense image while 50% was the same image where one of every two neighboring printed dots were omitted.

Example 1

The following ink composition formulations were made on a weight percentage basis and are offered as Examples.

TABLE 2

| Component | F712226 | F712227 | F712230 | F712312 | F712310 | G712454 |
|---|---|---|---|---|---|---|
| Acetone | 50.0 | 50.8 | 51.0 | 52.9 | 51.1 | 45.4 |
| Ethanol SDA23A | 39.0 | 40.4 | 39.2 | 40.5 | 39.1 | 41.3 |
| Diacetone alcohol | — | — | — | — | — | 3 |
| Propylene glycol | — | — | — | — | — | 0.5 |
| Deionized water | 5.0 | 5.0 | 5.0 | 2.0 | 2.0 | 2 |
| FD&C Blue #1 | 1.0 | 1.0 | — | — | — | — |
| Milijet blue 23 | — | — | 2.0 | 2.0 | 1.9 | 1.9 |
| Lithium nitrate | 1.0 | 1.0 | 1.0 | 0.6 | 0.6 | 0.6 |
| Ethocel, Std 4 (prem.) | 4.0 | — | — | — | — | — |
| Klucel EF | — | 1.8 | 1.8 | — | — | — |
| HPC SL | — | — | — | 2.0 | — | — |
| HPC SSL | — | — | — | — | 5.3 | 5.3 |
| Total weight percentage | 100.0 | 100.0 | 100.0 | 100.0 | 100.0 | 100.0 |
| Viscosity, cps | 3.0 | 2.9 | 3.0 | 3.0 | 3.3 | 5.6 |
| Resistivity, ohms cm | 376 | 356 | 377 | 535 | 553 | 607 |
| Velocity of sound, meters/second | 1216 | 1216 | 1216 | 1187 | 1184 | 1192 |

Acetone, diacetone alcohol and propylene glycol are commercially available from Ashland Chemical.
SDA-23A 200 proof denatured ethanol is available from LyondellBasell, Inc.
Deionized water is deionized water produced by reverse osmosis.
FD&C Blue #1 is Food Grade FD&C Blue number 1 available from Keystone Analine Corporation
Millijet Blue 28 is available from Milliken Chemical Corporation.
Lithium nitrate is available from FMC Lithum Division of Sigma Aldrich, Inc..
Klucel EF is hydroxypropylcellulose, available from Aqualon Corporation..
Ethocel Std. 4 isEthocel Standard 4 Premium grade and is ethyl cellulose, available from Dow Chemical Corporation.
HPC SL and SSL are hydroxypropylcellulose, available from Nisso America Corporation.

The ink compositions were filtered using ordinary methods used for inkjet printing. All properties were measured at a solution temperature of 25° C. As is seen from Table 2 above, all of the ink compositions possessed suitable viscosity, velocity of sound, and solution resistivity.

Example 2

Select ink compositions from Table 2 were tested for functional performance. Marks were printed with a Videojet 1510® CIJ printer in order to generate equivalent samples for comparative functional testing. The Videojet 1510® CIJ was selected as a good proxy for the binary array printer to perform preliminary comparative assessments of different ink compositions. The test substrate was the outer liner of Diaper 1, a semi-porous plastic film. The results are summarized in Table 3 below and compared against a Comparative Example ink V499-D, which is a commercially available wetness indicating ink for single nozzle continuous inkjet printers ink sold by Videojet Technologies.

TABLE 3

| Test Performed | V499-D (Comparative Example) | F712227 | F712230 | F712310 |
|---|---|---|---|---|
| Front layer contrast, visual scale | 2 | 2 | 2 | 2 |
| Dry time in seconds | 3.5 | 1.5 | 1.5 | 2 |
| Removability after 10 minutes aqueous exposure, visual scale. | 3 | 1 | 1 | 2 |

Visual scale: 1 = best; 5 = worst.

Approximate dry times were assessed by a light finger rub immediately after printing the marks. The table shows that the inventive ink compositions (F712227, F712230, and F712310) each showed far lower dry times than the Comparative Example. V499-D is an ethanol-based ink that includes a water soluble binder (PVP K30) and a water soluble dye but does not contain faster drying solvents like ketones. Removability was tested by soaking the printed marks in tap water with a pH of about 6.0. For each of the inventive ink compositions, color changes after soaking were visually assessed to be as good or better than the Comparative Example.

Example 3

Comparing the resins used in Example 1, resins Klucel EF and HPC SL exhibited measured molecular weight (Mw) values by GPC (gel permeation chromatography) of about 180 kDaltons and 120 kDaltons, respectively. F712310 included resin HPC SSL with a molecular weight of about 60 kDaltons. This ink composition was selected for further testing and loaded into a Videojet Binary Array BX6000 series printer. The printer was tested using simulated production conditions printing for 15 hours. The print quality remained consistent over this period when comparing test print samples from the start with the 15 hour end-point and no failures occurred that resulted in the interruption of printing. This test was repeated once and yielded the same result, demonstrating that F712310 could achieve a 15 hour run time. For comparison, ink F712230 employing Klucel EF was tested in two trials in the same printer. With the F712230 ink composition, each of the two trials achieved a maximum time under 3 hours prior to printhead failure. Failure in both cases occurred when the printer safety circuit automatically stopped operation due to an errant ink stream that splashed onto the printer high voltage plate and grounded the high voltage deflection circuit. Thus, it is apparent that the molecular weight of the binder used in the ink composition has a critical effect on the performance of the printer.

Example 4

The F712310 ink composition was further tested for degree of removability on various substrates. Two different images were printed with the F712310 ink composition using a BX6000 series printer, one image at 100% fill density and the other image at 50% fill density. These samples were soaked in tap water at a pH of 6.0 for 10 minutes and assessed colorimetrically (using the methods previously described) for their net color versus the background as shown in Table 4.

TABLE 4

| | | Initial samples | | | | After saline soak | | | | |
|---|---|---|---|---|---|---|---|---|---|---|
| Substrate | Fill density | L | a | b | ΔE from background | L | a | b | ΔE from background | % ΔE reduction |
| Diaper 1 | 50% | 84.6 | −16.7 | −15.7 | 24.1 | 92.7 | −5.0 | −6.1 | 7.8 | −67.5 |
| Diaper 1 | 100% | 76.0 | −30.1 | −25.5 | 42.8 | 90.0 | −11.7 | −10.2 | 15.7 | −63.4 |
| Diaper 2 | 50% | 77.9 | −17.3 | −15.2 | 25.1 | 88.8 | −2.5 | −2.6 | 2.8 | −88.9 |
| Diaper 3 | 50% | 82.7 | −23.2 | −16.9 | 30.5 | 93.5 | −3.1 | −2.8 | 3.6 | −88.1 |
| Diaper 3 | 100% | 75.7 | −31.2 | −24.3 | 43.3 | 92.8 | −4.8 | −3.8 | 5.8 | −86.6 |
| Diaper 4 | 50% | 83.4 | −20.3 | −16.3 | 27.2 | 94.4 | −1.0 | −2.6 | 1.2 | −95.5 |
| Diaper 4 | 100% | 73.4 | −30.1 | −20.1 | 41.9 | 94.4 | −1.0 | −2.7 | 1.3 | −96.9 |

While it was determined that the net degree of removal depended on the substrate, one of the three tested substrates at 100% fill density (Diaper 4) showed after soaking nearly visually imperceptible coloration (ΔE from background <2.0). Three substrates, Diapers 2, 3 and 4, at both 50% and 100% fill densities, showed some perceptible color remaining after soaking. However, the net reduction in coloration over the printed mark for each case was >80%, which would result in a visibly obvious change to an observer. In general, printing at 50% print densities (or less) provided best removability results with sufficiently high initial visual contrast through the outside of the film.

Example 5

Another test was conducted to compare an inventive printed image with a commercially available printed diaper image. A graphic image was printed using the ink composition G712354 of Table 2 at 50% print density onto the inner surface of the outer liner of the Diaper 5. The ink was printed side-by-side with an blue wetness indicator image previously printed by flexography onto the liner. The diaper absorbent material on the inner diaper surface was saturated with 1 cup of tap water at pH of 6.0 simulating an incontinence event and the liner was physically reattached to the wetted surface on the outer side. Both the inventive printed image and the commercially provided image were scrutinized for changes. Within about 10 seconds after reassembling the diaper, both images were distorted so badly by dissolution that they no longer resembled the parent image. Hence, the rates of change were essentially the same for the commercially provided blue mark and the inventive blue mark from ink composition G712354. It is apparent that diapers printed with the inventive ink composition printed by inkjet would function as a wetness indicator in a similar fashion as existing commercially available images that are not printed by inkjet.

Example 6

The dry times of ink composition F712310 were further evaluated by printing the ink composition with a BX printer onto Diaper 2 and a comparative hard thermoplastic polyethylene sheet. Images were printed at different image pixel densities passed in direct contact with and underneath a pickup roller at constant pressure as is provided in Table 4.

TABLE 4

| Substrate | Contact time (Seconds) | Average transfer ratings* Print density | | | |
|---|---|---|---|---|---|
| | | 100% | 75% | 50% | 25% |
| Hard polyethylene plastic | 0.25 | 5.0 | 5.0 | 5.0 | 5.0 |
| | 0.5 | 4.3 | 3.7 | 2.7 | 1.3 |
| | 0.75 | 3.0 | 3.0 | 2.0 | 1.0 |
| | 1 | 2.5 | 2.0 | 1.5 | 1.0 |
| | 1.33 | 2.0 | 1.0 | 1.0 | 1.0 |
| Diaper 2 | 0.1 | 5.0 | 5.0 | 5.0 | 4.0 |
| | 0.25 | 4.5 | 4.0 | 2.5 | 1.0 |
| | 0.5 | 4.3 | 3.3 | 2.0 | 1.0 |
| | 0.75 | 2.5 | 2.5 | 1.5 | 1.0 |
| | 1 | 1.0 | 1.0 | 1.0 | 1.0 |
| | 1.33 | 1.0 | 1.0 | 1.0 | 1.0 |

*Scale 1 = no transfer (fully dry); 5 = heavy transfer, image is fully readable on pickup roller.

The ambient conditions at the time of printing were approximately 23° C. and less than 40% relative humidity. Table 4 shows that for hard plastic substrates the unassisted dry time of F712310 is at best equal to or less than 0.75 seconds at 25% print density. In comparison, for the diaper film that is semi-porous (Diaper 2) the image dried in 1 second or less up to 100% print density at 128×128 dpi and dry times on a non-porous sheet were 0.1 second or less. For Diaper 2, dry times of 0.25 seconds or less were observed for 25% print density. Thus, it is apparent that the inventive ink compositions provide superior dry times than the dry times that can be achieved with current inks. Further, dry times as low as 0.25 seconds can be achieved in practice without physically assisted means, based on simply reducing the printed density.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of printing on a hygienic article comprising:
applying droplets of an ink composition with an ink jet printer to a surface of a hygienic article to form a desired image,
wherein the ink composition comprises:
an organic solvent selected from a ketone, an alcohol, or mixtures thereof;
a water-soluble binder resin comprising hydroxypropylcellulose with a molecular weight of between 10 kDaltons and 90 kDaltons; and
a water-soluble dye,
wherein the image acts as a wetness indicator by dissolving in an aqueous fluid.

2. The method of claim 1 wherein the ink composition has an unassisted dry time of 1 second or less at 100% print density and 128 by 128 dots per inch on the surface of the hygienic article.

3. The method of claim 1 wherein the ink composition has an unassisted dry time of 0.5 seconds or less at 25% print density and 128 by 128 dots per inch on the surface of the hygienic article.

4. The method of claim 1 wherein the ink jet printer is a binary array printer.

5. The method of claim 1 wherein the surface of the hygienic article is a plastic film.

6. The method of claim 5 wherein the plastic film is a semi-porous film.

7. The method of claim 1 wherein the surface of the hygienic article is a non-woven fabric.

8. The method of claim 7 wherein the ink composition provides an image on the hygienic article that is removed within 10 second after exposure to an aqueous medium.

9. The method of claim 1 wherein the image is printed in a single pass.

10. The method of claim 1 wherein the hygienic article moves with respect to the ink jet printer at a speed of greater than 2000 ft/min during printing.

11. The method of claim 1 wherein the solvent comprises acetone.

12. The method of claim 11 wherein the acetone is present in amount between 40% and 99% by weight of the ink composition.

13. The method of claim 12 further comprising ethanol in amount between 0.1% and 60% by weight of the ink composition.

14. The method of claim 1 further comprising water in an amount equal to or less than 5% by weight of the ink composition.

15. The method of claim 1 wherein the dye is substantially soluble in water at a temperature of 20 to 40° C. and pH of between 4 and 9.

16. The method of claim 1 wherein the resin is substantially soluble in water at a temperature of 20 to 40° C. and pH of between 4 and 9.

17. The method of claim 1 wherein the ink composition is substantially free of solid particle sized greater than 1 micron.

18. The method of claim 1 wherein the dye is selected from polymeric dyes and dyes classified as FD&C colorants or D&C colorants in the U.S or their foreign variants approved for food, cosmetic or drug usage.

19. The ink composition of claim 18 wherein the dye is selected from FD&C Blue #1 and a blue triarylmethane chromophore dye.

20. A hygienic article comprising:
a body contacting surface;
a garment contacting surface opposite the body contacting surface;
and
an image printed by ink jet printing which is visible through either the body contacting surface or the garment contacting surface, wherein the image is formed from an ink composition comprising a water-soluble dye and a water-soluble resin comprising hydroxypropylcellulose with a molecular weight of between 10 kDaltons and 90 kDaltons, wherein the image provides a wetness indicator.

21. The article of claim 20 wherein the dye is selected from FD&C Blue #1, a blue triarylmethane chromophore dye, and mixtures thereof.

22. An ink jet ink composition comprising:
a solvent comprising acetone in amount between 40% and 99% by weight of the ink composition and ethanol in amount between 0.1% and 60% by weight of the ink composition;
a water-soluble binder resin comprising hydroxypropylcellulose with a molecular weight of between 10 kDaltons and 90 kDaltons; and
a water-soluble dye selected from FD&C Blue #1 and a blue triarylmethane chromophore dye, wherein the ink composition has a dry time of less than 0.5 seconds when printed on a semi-porous surface using a binary array printer.

\* \* \* \* \*